US010357332B2

(12) United States Patent
Kuun (10) Patent No.: US 10,357,332 B2
(45) Date of Patent: Jul. 23, 2019

(54) DEPTH ADJUSTABLE SURGICAL PIN

(71) Applicant: Thomas Kuun, Tonawanda, NY (US)

(72) Inventor: Thomas Kuun, Tonawanda, NY (US)

( * ) Notice: Subject to any disclaimer, the term of this patent is extended or adjusted under 35 U.S.C. 154(b) by 202 days.

(21) Appl. No.: 15/371,777

(22) Filed: Dec. 7, 2016

(65) Prior Publication Data

US 2018/0153563 A1    Jun. 7, 2018

(51) Int. Cl.
*A61B 17/17*    (2006.01)
*A61C 1/08*    (2006.01)
*A61C 8/00*    (2006.01)

(52) U.S. Cl.
CPC .............. *A61C 1/084* (2013.01); *A61C 8/001* (2013.01); *A61C 8/0089* (2013.01)

(58) Field of Classification Search
CPC ....................................................... A61B 17/17
See application file for complete search history.

(56) References Cited

U.S. PATENT DOCUMENTS

| 4,383,527 A | 5/1983 | Asnis et al. | |
|---|---|---|---|
| 6,282,187 B1 | 8/2001 | Evans | |
| 7,001,333 B2 * | 2/2006 | Hamel | A61B 1/32 600/208 |
| 2009/0105769 A1 | 4/2009 | Rock et al. | |
| 2010/0145142 A1 * | 6/2010 | Begemann | A61B 17/3421 600/104 |
| 2010/0305621 A1 | 12/2010 | Wang et al. | |
| 2014/0171946 A1 * | 6/2014 | Benson | A61B 17/1655 606/79 |

* cited by examiner

*Primary Examiner* — Christopher J Beccia
(74) *Attorney, Agent, or Firm* — Vincent G. LoTempio; Kloss, Stenger & LoTempio; David T. Stephenson (57) ABSTRACT

A depth adjustable surgical pin retains a surgical template at a desired depth, vertical and horizontal position, and pressure against an organic substrate. The surgical pin provides a housing and a retention rod that work in conjunction to achieve this retention function. The housing is defined by a mount end, rod end, inner sidewall having a female thread, and an outer sidewall having ridges for adhering to a drill guide aperture of the surgical template. The housing sets at a predetermined depth in the drill guide aperture. The retention rod comprises a proximal end having a cap, distal end tapering to a sharp point, and a male thread that threadably engages the housing. The retention rod serves as an anchor and provides added strength to the surgical template. The housing becomes an integral part of the surgical guide template to guide the retention rod into a locking position.

20 Claims, 5 Drawing Sheets

DEPTH ADJUSTABLE SURGICAL PIN

FIELD OF THE INVENTION

The present invention relates generally to a depth adjustable surgical pin. More so, a depth adjustable surgical pin is configured to help retain a surgical template at a desired depth, vertical and horizontal position, and pressure against an organic substrate through use of a housing and a retention rod that work in conjunction; whereby the housing integrates into at least one drill guide aperture of the surgical template at a predetermined depth to guide a surgical tool into the organic substrate at the precise predetermined depth; whereby the retention rod threadably engages the housing to penetrate into the organic substrate, and thereby lock the surgical guide tool at the desired vertical and horizontal position and pressure against the organic substrate, pre-surgery in preparation for the rest of the surgical procedure to follow.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

It is known that dental surgery involves any of a number of medical procedures that involve artificially modifying dentition. Dental surgery can include surgery of the teeth and jaw bones. One common type of dental surgery involves integrating dental implants into the jawbone to replace missing teeth in a patient's mouth using various procedures.

Typically, surgery for dental implantation requires careful pre-surgical evaluation regarding multiple aspects. For example, alveolar space, bone density of the alveolar bone, the condition of the gum, and positioning of the roots of neighboring teeth, are parameters to be evaluated for determining a suitable dental implant and the depth and angle for implementing the dental implant.

Often, these types of dental implant procedures involve drilling a pilot hole into the jawbone of a patient and inserting an implant body into the hole provided. The crown is then cemented to the top section of the implant abutment to complete the procedure. There are various prior art stents used as drill guides for drilling the initial pilot hole.

In many instances, a surgical guide template is placed over the teeth to help guide the drill at the precise location of the pilot hole. The surgical guide template is required to be anchored into place, so as to prevent slippage and misalignment during surgery. Specifically, the apertures in the surgical guide template must align directly above the pilot holes. A surgical guide pin may be used to help lock the surgical guide template against the jaw bone, so as to align the guide apertures with the pilot holes.

Other proposals have involved surgical pins that help retain surgical templates against bone or tissue. The problem with these surgical pins is that they do not control the depth, position, and pressure of the surgical template against the bone or tissue. Even though the above cited gripping devices meets some of the needs of the market, a depth adjustable surgical pin is configured to help retain a surgical template at a desired depth, vertical and horizontal position, and pressure against an organic substrate through use of a housing and a retention rod that work in conjunction is still desired.

SUMMARY OF THE INVENTION

The present invention is directed to a depth adjustable surgical pin used to retain a surgical template at a desired depth, vertical and horizontal position, and pressure against an organic substrate, pre-surgery in preparation for the rest of the surgical procedure to follow. The depth adjustable surgical pin is configured to adjustably retain the surgical template at a desired vertical and horizontal position, as well as a determined pressure against the organic substrate. The depth adjustable surgical pin provides a housing and a retention rod that work in conjunction to achieve this retention function for the surgical template.

In some embodiments, the housing integrates into at least one drill guide aperture of the surgical template. The housing is configured to utilize friction, adhesion, and fasteners to form a secure, locked integration with the drill guide aperture. The housing sets at a predetermined depth in relation to the drill guide aperture. In this manner, a surgical tool may pass through openings in the surgical template and penetrate the organic substrate at the precise predetermined depth set by the housing.

In some embodiments, the retention rod is configured to pass through, and threadably engage the housing. The position of the retention rod in relation to the integrated housing dictates the depth, position, and pressure of the surgical template in relation to the organic substrate. The retention rod serves as an anchor and provides added strength to the surgical template. The housing thus becomes an integral part of the surgical guide template, so as to guide the retention rod into a locking position. The locking position retains the surgical guide template at the desired depth, vertical and horizontal position, and pressure in relation to the organic substrate.

The retention rod is defined by a threaded section having a rod thread. The rod thread may include a male thread. The rod thread rotatably engages a housing thread of the housing. The retention rod is further defined by a tapered distal end that terminates at a sharp point to enable at least partial penetration into the organic substrate. In this manner, the retention rod may be rotatably urged through the housing to penetrate the organic substrate; thereby locking the surgical guide tool at the desired depth, vertical and horizontal position, and pressure against the organic substrate.

Thus, in the final locked position: the rod thread is set against the housing thread; the cap of the retention rod is set against the lip of the housing; and the surgical template is set against the organic template, at the desired depth, position, and pressure. In this manner, the surgical template may be adjusted more precisely against the organic substrate. This unique engagement between the housing, the retention rod, and the surgical template enables for more precise and controllable surgical procedures.

One aspect of a depth adjustable surgical guide pin, comprises:

a housing, the housing defined by a generally annular shape, the housing further defined by a mount end and a rod end, the rod end having a lip, the housing further defined by an inner sidewall and an outer sidewall, the inner sidewall having a housing thread, the outer sidewall having a plurality of ridges, the plurality of ridges of the outer sidewall configured to enable an enhanced grip; and a generally elongated retention rod, the retention rod defined by a longitudinal axis, the retention rod further defined by a proximal end, a distal end, and a threaded section, the proximal end having a cap, the cap disposed generally perpendicular to the longitudinal axis, the distal end defined by a generally tapered configuration terminating at a generally sharp point, the threaded section having a rod thread, whereby the rod thread of the retention rod is configured to rotatably engage the housing thread of the housing, whereby rotation of the retention rod in a first direction axially displaces the retention rod towards the mount end of the housing, whereby rotation of the retention rod in a second direction axially displaces the retention rod towards the rod end of the housing.

In another aspect, the lip is disposed generally perpendicular to the rod end of the housing.

In another aspect, the lip extends outwardly towards the outer sidewall of the housing.

In yet another aspect, the lip of the housing is configured to engage the cap of the retention rod.

In yet another aspect, the plurality of ridges are disposed in a generally spaced-apart, circular configuration on the outer sidewall of the housing.

In yet another aspect, the housing thread is a female thread.

In yet another aspect, the rod thread is a male thread.

In yet another aspect, the proximal end of the retention rod has a larger diameter than the distal end of the retention rod.

In yet another aspect, threaded section of the retention rod is more proximally disposed to the proximal end of the retention rod.

In yet another aspect, the housing is configured to enable setting in at least one drill guide aperture of a surgical guide template.

In yet another aspect, the retention rod is configured to enable anchoring of the surgical guide template in an organic substrate at an adjustable depth, vertical and horizontal position, and pressure against the organic substrate.

It is one objective of the present invention to provide a depth adjustable surgical guide pin that anchors a surgical guide template at a desired depth, vertical and horizontal position, and pressure against an organic substrate.

It is another objective to enable the depth, position, and pressure of the surgical template to be adjusted through rotation of the retention rod against the housing.

It is another objective to provide a housing that becomes an integral part of the surgical guide template, so as to help guide the retention rod into a locking position.

It is another objective to lock the surgical guide template at a desired depth, vertical and horizontal position, and pressure in relation to the organic substrate.

It is another objective to provide the plurality of ridges along the outer sidewall of the housing that can work in conjunction with an adhesive to enhance adhesion, so that the housing integrate into the drill guide aperture of the surgical template.

Yet another objective is to create a stable positive locking mechanism for a surgeon to perform a precise surgical procedure and to maximize a positive outcome in guided surgical procedures.

Yet another objective is to provide an inexpensive to manufacture depth adjustable surgical pin.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIGS. 5A and 5B illustrate a close up view of the depth adjustable surgical pin in FIG. 1, being operational with an exemplary surgical template, where FIG. 5B illustrates the retention rod rotatably being displaced into the housing, and FIG. 5B illustrates the retention rod in a locked position against the surgical template, in accordance with an embodiment of the present invention.

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

FIGS. 1-5B illustrate a depth adjustable surgical pin 100. The depth adjustable surgical pin 100, hereafter, "surgical pin 100" is configured to help retain a surgical template 400 at a desired depth, vertical and horizontal positon, and pressure against an organic substrate. Those skilled in the art will recognize that retaining the surgical template 400 at the desired position against the organic tissue is generally accomplished pre-surgery, in preparation for the rest of the surgical procedure to follow. The surgical pin 100 is efficacious for locking the surgical template at a precise and secure position against the organic substrate. In some embodiments, the organic substrate may include, without limitation, a bone, tissue, a jawbone, teeth, muscle, and cartilage. In other embodiments, the surgical pin 100 may be used for dental surgery, such as setting implants into the teeth.

The depth adjustable surgical pin 100 is configured to adjustably retain the surgical template 400 at the desired depth, vertical and horizontal position, and pressure against the organic substrate. This is achieved through rotatable manipulation of the surgical pin, which allows for precise and controllable adjustability. The depth may be adjusted to move the surgical template 400 proximally and distally from the organic substrate. Further, the tilt angle of the surgical template 400 in relation to the organic substrate may be adjusted. The vertical and horizontal positon may also be adjusted to align with predrilled pilot holes, or other guide holes known in the art.

Further, the pressure of the surgical template 400 against the organic substrate may be adjusted. The pressure may be adjusted to fasten and remove the surgical template 400 in relation to the organic substrate, as needed. In some embodiments, the surgical template 400 may include a malleable, resinous, thermoplastic base that is shaped substantially in the form of the teeth and jawbone. The surgical template 400 may include a base having an inner and outer surface, and at least one drill guide aperture 402. The drill guide aperture is configured to receive the surgical pin 100.

Figure 1:
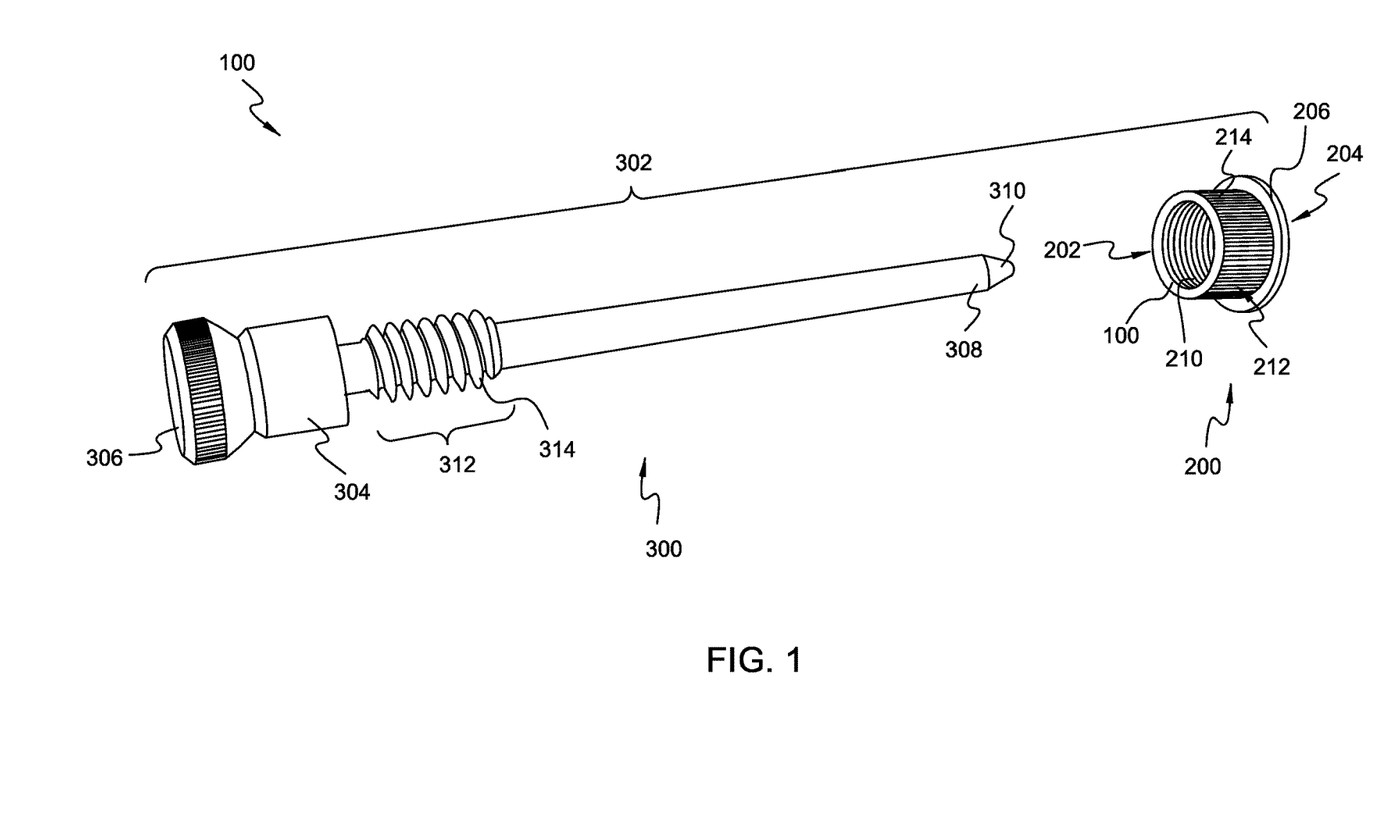
FIG. 1 illustrates a side perspective view of an exemplary depth adjustable surgical pin, showing an exemplary housing and an exemplary retention rod separate, in accordance with an embodiment of the present invention.

As FIG. 1 references, the surgical pin 100 provides a housing 200 and a retention rod 300 that work in conjunction, through a threaded engagement, to securely and adjustably retain the surgical template 400 against the organic substrate. In some embodiments, the housing 200 integrates into the at least one drill guide aperture 402 of the surgical template 400. The housing 200 is configured to utilize friction, adhesion, and fasteners for integrating into the drill guide aperture 402. The housing 200 sets at a predetermined depth in the drill guide aperture 402. In this manner, a surgical tool may pass through openings in the surgical template 400 and penetrate the organic substrate at the precise predetermined depth set by the housing 200.

In some embodiments, the housing 200 may be defined by a generally annular shape. The shape and size of the housing is generally slightly smaller than the drill guide aperture 402, so as to form a snug integration with the surgical template 400. The housing 200 may further include a mount end 202 and a rod end 204. The rod end 204 forms a lip 206 that circles around the housing 200. The lip 206 is disposed generally perpendicular to the rod end 204 of the housing 200.

In some embodiments, the housing 200 may further include an inner sidewall 208 and an outer sidewall 212. The inner sidewall 208 comprises a housing thread 210. In one embodiment, the housing thread 210 is a female thread. The outer sidewall 212 comprises a plurality of ridges 214 that form an equal, spaced-apart configuration. The ridges 214 are configured to help adhere the housing 200 to the drill guide aperture 402 of the surgical template 400. In one embodiment, an adhesive coats the ridges 214, so as to strengthen the frictional engagement between the housing 200 and the drill guide aperture 402.

Figure 2:
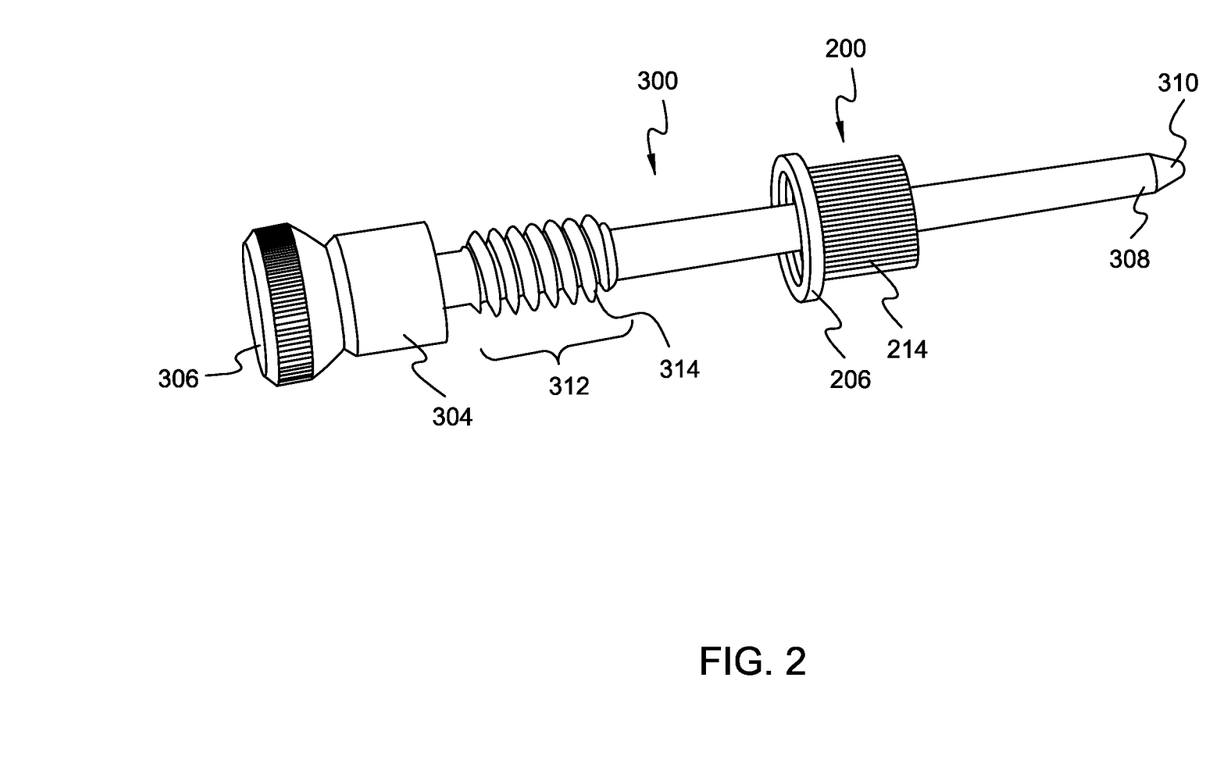
FIG. 2 illustrates a side perspective view of the depth adjustable surgical pin in FIG. 1, showing the retention rod passing through the housing, in accordance with an embodiment of the present invention.

Turning now to FIG. 2, the retention rod 300 is configured to pass through, and threadably engage the housing 200. The position of the retention rod 300 in relation to the integrated housing 200 dictates the depth, position, and pressure of the surgical template 400 in relation to the organic substrate. The retention rod 300 serves as an anchor and provides added strength to the surgical template 400. The retention rod 300 also rotatably engages the housing 200 so as to lock the surgical temple at the desired depth, positon, and pressure against the organic substrate. The housing 200, thus becomes an integral part of the surgical template 400, so as to guide the retention rod 300 into a locking position. The locking position retains the surgical template 400 at the desired depth, vertical and horizontal position, and pressure in relation to the organic substrate.

The retention rod 300 is generally elongated, forming a longitudinal axis 302 that has sufficient length to pass through the housing 200 and at least partially penetrate the organic substrate. The retention rod 300 is defined by a proximal end 304, a distal end 308, and a threaded section 312. The proximal end 304 is the end that enables rotatable manipulation of the retention rod 300. The proximal end 304 of the retention rod 300 has a larger diameter than the distal end 308 of the retention rod 300. In one embodiment, the proximal end 304 forms a sheath that when engaging the inner sidewall 208 of the housing 200, restricts passage of the retention rod 300 through the housing 200, and further towards the organic substrate.

As was illustrated in FIGS. 1 and 2, the proximal end 304 of the retention rod 300 comprises a cap 306. The cap 306 may be generally circular in shape and have a defined thickness. The cap 306 may also be configured to engage the lip 206 of the housing 200, so as to restrict movement of the retention rod 300 towards the organic substrate. The cap 306 may be configured to enable rotation of the retention rod 300 against the housing 200. Specifically, the cap 306 is disposed generally perpendicular to the longitudinal axis, and may include a slot, so that an instrument may rotatably urge the retention rod 300 through the cap 306.

In some embodiments, the distal end 308 of the retention rod 300 is defined by a generally tapered configuration terminating at a generally sharp point 310. The sharp point 310 is configured to at least partially penetrate the organic substrate.

The retention rod 300 is further defined by a threaded section 312. In one embodiment, the threaded section 312 of the retention rod 300 is more proximally disposed to the proximal end 304 of the retention rod 300. The threaded section 312 may include a rod thread 314 that is configured to threadably engage the housing thread 210 of the housing 200. In one embodiment, the rod thread 314 is a male thread that is configured to mate with, and enable displacement against the housing thread 210, i.e., female thread, of the inner sidewall 208 of the housing 200. In this manner, the retention rod 300 may be rotatably urged through the housing 200 to penetrate the organic substrate; thereby locking the surgical guide tool at the desired depth, vertical and horizontal position, and pressure against the organic substrate.

Figure 3:
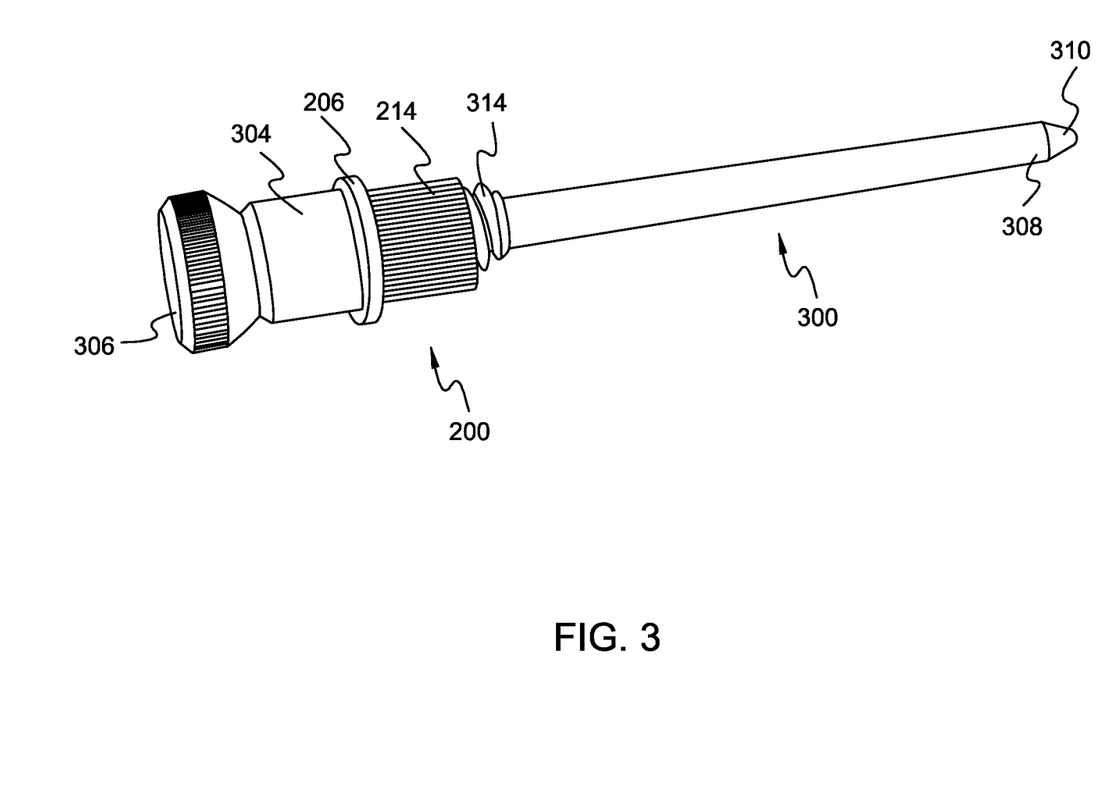
FIG. 3 illustrates a side perspective view of the depth adjustable surgical pin in FIG. 1, showing the retention rod and the housing threadably fastened together, in accordance with an embodiment of the present invention.

In one exemplary embodiment shown in FIG. 3, the rod thread 314 of the retention rod 300 is configured to rotatably engage the housing thread 210 of the housing 200, whereby rotation of the retention rod 300 in a first direction displaces the retention rod 300 towards the mount end 202 of the housing 200. This tightens the surgical pin 100 against the surgical template 400.

Conversely, rotation of the retention rod 300 in a second direction displaces the retention rod 300 towards the rod end 204 of the housing 200. This loosens the surgical pin 100 from the surgical template 400. In this manner, the retention rod 300 may easily move in and out of the housing 200, and in and out of penetration of the organic substrate. This unique engagement between the surgical template 400, the housing 200, and the retention rod 300 enables for more precise and controllable surgical procedures.

Figure 4:
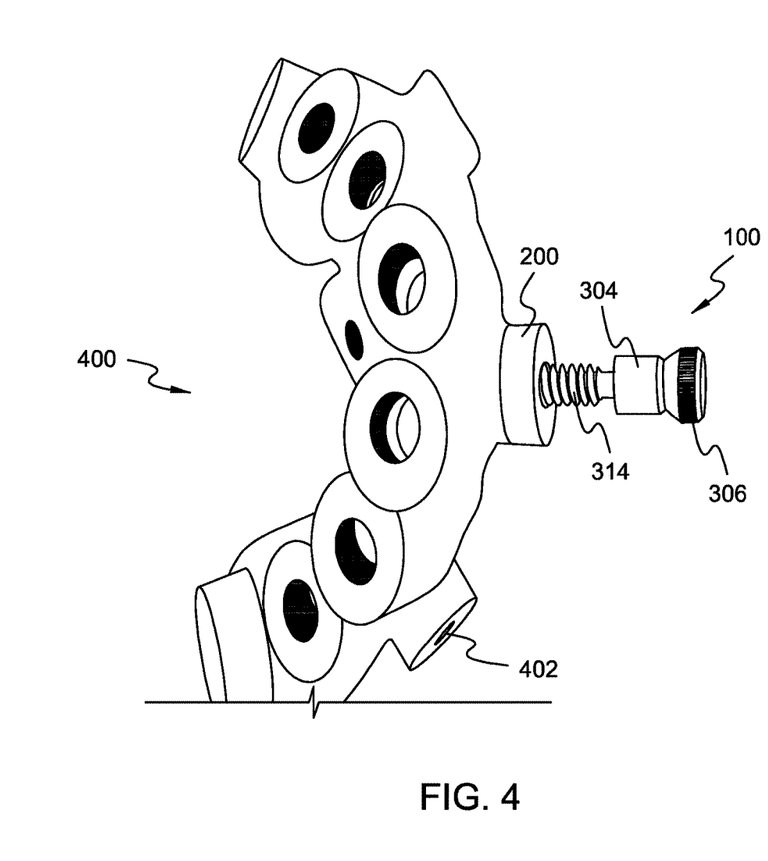
FIG. 4 illustrates a side perspective view of the depth adjustable surgical pin in FIG. 1, being operational with an exemplary surgical template, showing the housing integrated into the surgical template and the retention rod engaging the housing, in accordance with an embodiment of the present invention.

Operation of the surgical pin 100 is illustrated in FIG. 4. As illustrated, the housing 200 is configured to enable setting in at least one drill guide aperture 402 of a surgical guide template. This forms the foundation for the surgical pin 100, and also creates a reference point for the depth, vertical and horizontal position, and pressure against the organic substrate. The retention rod 300 is configured to enable anchoring of the surgical template 400 in an organic substrate at an adjustable depth, vertical and horizontal position, and pressure against the organic substrate.

Figure 5A:
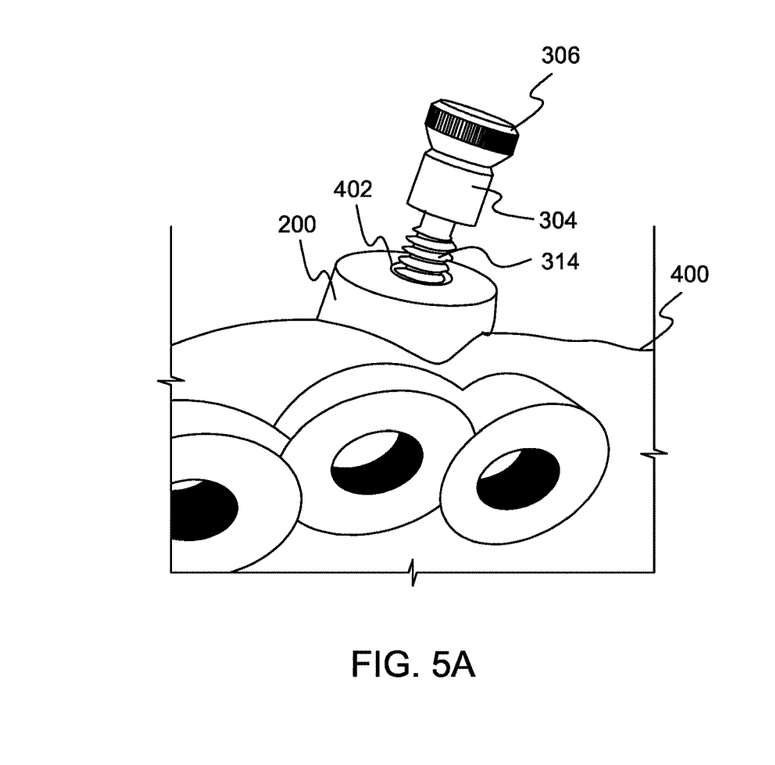

Looking now at FIG. 5A, the retention rod 300 rotatably engages the housing thread 210 of the housing 200 in a first direction. This causes displacement of the retention rod 300 towards the mount end 202 of the housing 200. As a desired depth, vertical and horizontal position, and pressure against the organic substrate rotation is achieved, rotation of the retention rod 300 is ceased. However, the direction of the rotation may also be reversed in the second direction to compensate for excessive tightening of the retention rod 300 or to remove the surgical template 400 post-surgery.

Figure 5B:
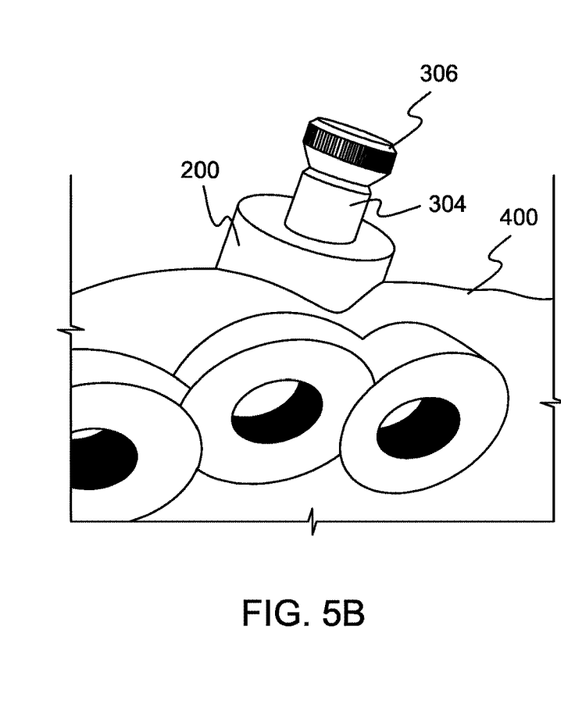

Thus, as FIG. 5B illustrates: the rod thread 314 is set against the housing thread 210; the cap 306 of the retention rod 300 is set against the lip 206 of the housing 200; and the surgical template 400 is set against the organic template, at the desired depth, position, and pressure. In this manner, the surgical template 400 may be adjusted more precisely against the organic substrate.

These and other advantages of the invention will be further understood and appreciated by those skilled in the art by reference to the following written specification, claims and appended drawings.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What I claim is:

1. A depth adjustable surgical guide pin, the guide pin comprising:
    a housing, the housing defined by a generally annular shape, the housing further defined by a mount end and a rod end, the rod end having a lip, the housing further defined by an inner sidewall and an outer sidewall, the inner sidewall having a housing thread, the outer sidewall having a plurality of ridges, wherein the plurality of ridges are positioned adjacent the housing thread on the housing such that the plurality of ridges and the housing thread overlap on a latitudinal axis of the housing, wherein the plurality of ridges, the housing thread and the lip are part of an integral unit with the housing, the plurality of ridges of the outer sidewall configured to enable an enhanced grip; and
    a generally elongated retention rod, the retention rod defined by a longitudinal axis, the retention rod further defined by a proximal end, a distal end, and a threaded section, the proximal end having a cap, the cap disposed generally perpendicular to the longitudinal axis, the distal end defined by a generally tapered configuration terminating at a generally sharp point, the threaded section having a rod thread,
    whereby the rod thread of the retention rod is configured to rotatably engage the housing thread of the housing, whereby rotation of the retention rod in a first direction axially displaces the retention rod towards the mount end of the housing, whereby rotation of the retention rod in a second direction axially displaces the retention rod towards the rod end of the housing.

2. The guide pin of claim 1, wherein the lip is disposed generally perpendicular to the rod end of the housing.

3. The guide pin of claim 1, wherein the lip extends outwardly towards the outer sidewall of the housing.

4. The guide pin of claim 1, wherein the lip of the housing is configured to engage the cap of the retention rod.

5. The guide pin of claim 1, wherein the plurality of ridges are disposed in a generally spaced-apart, circular configuration on the outer sidewall of the housing.

6. The guide pin of claim 1, wherein the housing thread is a female thread.

7. The guide pin of claim 1, wherein the rod thread is a male thread.

8. The guide pin of claim 1, wherein the proximal end of the retention rod has a larger diameter than the distal end of the retention rod.

9. The guide pin of claim 1, wherein the threaded section of the retention rod is more proximally disposed to the proximal end of the retention rod.

10. The guide pin of claim 1, wherein the housing is configured to integrate into at least one drill guide aperture of a surgical guide template.

11. The guide pin of claim 10, wherein the retention rod is configured to enable anchoring of the surgical guide template in an organic substrate at a depth, a vertical and horizontal position, and a pressure.

12. A depth adjustable surgical guide pin, the guide pin comprising:
    a housing, the housing defined by a generally annular shape, the housing further defined by a mount end and a rod end, the rod end having a lip, the housing further defined by an inner sidewall and an outer sidewall, the inner sidewall having a housing thread, the outer sidewall having a plurality of ridges;
    a generally elongated retention rod, the retention rod defined by a longitudinal axis, the retention rod further defined by a proximal end, a distal end, and a threaded section, the proximal end having a cap, the cap disposed generally perpendicular to the longitudinal axis, the distal end defined by a generally tapered configuration terminating at a generally sharp point, the threaded section having a rod thread,
    whereby the rod thread of the retention rod is configured to rotatably engage the housing thread of the housing, whereby rotation of the retention rod in a first direction displaces the retention rod towards the mount end of the housing, whereby rotation of the retention rod in a second direction displaces the retention rod towards the rod end of the housing; and
    a surgical template, the surgical template configured to enable engagement with an organic substrate at a depth, a position, and a pressure, whereby displacement of the retention rod towards the mount end of the housing, and displacement of the retention rod towards the rod end of the housing enables adjustment of the surgical template in relation to the organic substrate, the surgical template defined by at least one drill guide aperture, the at least one drill guide aperture configured to receive the housing, whereby the plurality of ridges of the outer sidewall are configured to enable enhanced grip to the surgical template within the at least one drill guide aperture of the surgical template.

13. The guide pin of claim 12, wherein the lip is disposed generally perpendicular to the rod end of the housing.

14. The guide pin of claim 12, wherein the lip extends outwardly towards the outer sidewall of the housing.

15. The guide pin of claim 12, wherein the lip of the housing is configured to engage the cap of the retention rod.

16. The guide pin of claim 12, wherein the plurality of ridges are disposed in a generally spaced-apart, circular configuration on the outer sidewall of the housing.

17. The guide pin of claim 12, wherein the housing thread is a female thread.

18. The guide pin of claim 12, wherein the rod thread is a male thread.

19. The guide pin of claim 12, wherein the proximal end of the retention rod has a larger diameter than the distal end of the retention rod.

20. The guide pin of claim 12, wherein the threaded section of the retention rod is more proximally disposed to the proximal end of the retention rod.

* * * * *